(12) United States Patent
Wilmott et al.

(10) Patent No.: US 12,409,111 B2
(45) Date of Patent: Sep. 9, 2025

(54) SYSTEM, METHOD, AND COMPOSITION FOR SKIN IMPROVEMENT AND TRANSIENT FLORA REDUCTION

(71) Applicant: LEADING EDGE INNOVATIONS, LLC, Branchburg, NJ (US)

(72) Inventors: James Michael Wilmott, Bangor, PA (US); Michael Alan Ross, Nazareth, PA (US)

(73) Assignee: LEADING EDGE INNOVATIONS, LLC, Branchburg, NJ (US)

( * ) Notice: Subject to any disclaimer, the term of this patent is extended or adjusted under 35 U.S.C. 154(b) by 0 days.

(21) Appl. No.: 17/512,251

(22) Filed: Oct. 27, 2021

(65) Prior Publication Data

US 2022/0125691 A1  Apr. 28, 2022

Related U.S. Application Data

(60) Provisional application No. 63/106,208, filed on Oct. 27, 2020.

(51) Int. Cl.
| | |
|---|---|
| A61K 8/06 | (2006.01) |
| A61Q 19/00 | (2006.01) |
| B01F 23/41 | (2022.01) |

(52) U.S. Cl.
CPC ............ *A61K 8/064* (2013.01); *A61Q 19/00* (2013.01); *B01F 23/4105* (2022.01); *B01F 23/4145* (2022.01); *A61K 2800/413* (2013.01)

(58) Field of Classification Search
None
See application file for complete search history.

(56) References Cited

U.S. PATENT DOCUMENTS

| | | |
|---|---|---|
| 2,217,698 A | 10/1940 | Musher |
| 3,208,911 A | 9/1965 | Oppliger |
| 3,964,500 A | 6/1976 | Drakoff |
| 4,152,416 A | 5/1979 | Spitzer et al. |
| 4,341,799 A | 7/1982 | Good |
| 4,364,837 A | 12/1982 | Pader |
| 4,465,619 A | 8/1984 | Boskamp |
| 4,592,859 A | 6/1986 | Smith-Johannsen |
| 4,606,913 A | 8/1986 | Aronson et al. |
| 4,720,390 A | 1/1988 | Bachler et al. |
| 4,788,006 A | 11/1988 | Bolich, Jr. et al. |
| 4,952,859 A | 8/1990 | Torisawa et al. |
| 5,011,701 A | 4/1991 | Baer et al. |
| 5,021,248 A | 6/1991 | Stark et al. |
| 5,330,778 A | 7/1994 | Stark et al. |
| 5,425,956 A | 6/1995 | Shahidi et al. |
| 5,637,291 A | 6/1997 | Bara et al. |
| 5,688,528 A | 11/1997 | Carlsson et al. |
| 5,716,638 A | 2/1998 | Touitou |
| 5,928,632 A | 7/1999 | Reusch |
| 5,928,832 A | 7/1999 | Smith et al. |
| 6,068,961 A | 5/2000 | Dutoff et al. |
| 6,190,686 B1 | 2/2001 | Isager et al. |
| 6,268,102 B1 | 7/2001 | Hopper et al. |
| 6,391,321 B1 | 5/2002 | Gers-Barlag et al. |
| 6,423,363 B1 | 7/2002 | Traska et al. |
| 6,436,413 B1 | 8/2002 | Gers-Barlag et al. |
| 6,485,756 B1 | 11/2002 | Aust et al. |
| 6,782,307 B2 | 8/2004 | Wilmott et al. |
| 6,863,914 B1 | 3/2005 | Auweter |
| 7,250,455 B2 | 7/2007 | Cody et al. |
| 7,270,832 B2 | 9/2007 | Bryson et al. |
| 7,306,819 B2 | 12/2007 | Lerchenfeld et al. |
| 7,709,445 B2 | 5/2010 | Soula et al. |
| 8,034,381 B2 | 10/2011 | Moschwitzer |
| 8,068,961 B2 | 11/2011 | Menze et al. |
| 8,114,386 B2 | 2/2012 | Kantner et al. |
| 8,597,678 B2 | 12/2013 | Fountain et al. |
| 8,618,081 B2 | 12/2013 | Tamarkin et al. |
| 9,357,770 B2 | 6/2016 | Wilmott et al. |
| 2002/0127257 A1 | 9/2002 | Gers-Barlag et al. |
| 2002/0146375 A1 | 10/2002 | Schreiber et al. |
| 2003/0021547 A1 | 1/2003 | Bolle et al. |
| 2003/0215470 A1 | 11/2003 | Wilmott et al. |
| 2003/0215471 A1 | 11/2003 | Wilmott et al. |
| 2003/0228267 A1 | 12/2003 | Aust et al. |

(Continued)

FOREIGN PATENT DOCUMENTS

| | | |
|---|---|---|
| AU | 2011213719 A1 | 3/2013 |
| CN | 1125145 A | 6/1996 |

(Continued)

OTHER PUBLICATIONS

PE2E translation of CN-111629789-A, Sep. 2020 (Year: 2020).*
Dicitonary.com, Definition of Room Temperature, https://www.dictionary.com/browse/room-temperature, Retrieved online Feb. 28, 2023, (Year: 2023).*
Glycerol; Wikipedia article; Retrieved from "https://en.wikipedia.org/w/index.php?title=Glycerol&oldid=9833894125"; published on Oct. 14, 2020, Abstract on p. 1.

(Continued)

*Primary Examiner* — Jennifer A Berrios
(74) *Attorney, Agent, or Firm* — OHLANDT, GREELEY AND PERLE, L.L.P.

(57) ABSTRACT

A composition for reducing transient flora on skin and improving the condition of the skin includes Ethanol or Isopropanol in an amount that is in a range from at least 60% to about 95% v/v of the composition and a hydrophobe-in-water dispersion. The composition can be prepared by homogenizing and high-pressure high-shearing a mixture of water, humectants, and one or more hydrophobes to form a hydrophobe-in-water dispersion, separately preparing an aqueous medium having the ethanol or isopropanol, and combining hydrophobe-in-water dispersion with the aqueous medium.

27 Claims, 1 Drawing Sheet

(56) References Cited

U.S. PATENT DOCUMENTS

| | | |
|---|---|---|
| 2004/0082654 A1 | 4/2004 | Pesce et al. |
| 2005/0065239 A1 | 3/2005 | Cody et al. |
| 2005/0266055 A1 | 12/2005 | Stiller et al. |
| 2007/0023779 A1 | 2/2007 | Hirose et al. |
| 2007/0087022 A1 | 4/2007 | Desai et al. |
| 2007/0104665 A1 | 5/2007 | Jones et al. |
| 2007/0116761 A1 | 5/2007 | Desai et al. |
| 2007/0122465 A1 | 5/2007 | Desai et al. |
| 2007/0122468 A1 | 5/2007 | Desai et al. |
| 2007/0154539 A1 | 7/2007 | Fountain et al. |
| 2007/0237798 A1 | 10/2007 | Apostol et al. |
| 2007/0264295 A1 | 11/2007 | Kantner |
| 2008/0075808 A1 | 3/2008 | Altemueller |
| 2008/0093586 A1 | 4/2008 | Koch et al. |
| 2008/0102128 A1 | 5/2008 | Constancis et al. |
| 2008/0274195 A1 | 11/2008 | Nicolosi et al. |
| 2009/0004278 A1 | 1/2009 | Aimi et al. |
| 2009/0019697 A1 | 1/2009 | Dodd |
| 2009/0155409 A1 | 6/2009 | Sexton et al. |
| 2009/0196972 A1 | 8/2009 | Monsalve-Gonzalez et al. |
| 2009/0226498 A1 | 9/2009 | Flugge-Berendes et al. |
| 2009/0280148 A1 | 11/2009 | Aimi et al. |
| 2010/0143424 A1 | 6/2010 | Kanazawa |
| 2010/0203121 A1 | 8/2010 | Toledano et al. |
| 2010/0264364 A1 | 10/2010 | Wagner et al. |
| 2010/0285113 A1 | 11/2010 | Shoichet et al. |
| 2010/0305218 A1 | 12/2010 | Wooster et al. |
| 2010/0323014 A1 | 12/2010 | Bloom et al. |
| 2011/0281827 A1 | 11/2011 | Tamarkin et al. |
| 2011/0305737 A1 | 12/2011 | Alexiades-Armenakas et al. |
| 2012/0027865 A1 | 2/2012 | Sahoo et al. |
| 2012/0093718 A1 | 4/2012 | Parchment et al. |
| 2012/0244134 A1 | 9/2012 | Chen et al. |
| 2012/0308627 A1 | 12/2012 | Gunes et al. |
| 2013/0004640 A1 | 1/2013 | Zhang et al. |
| 2013/0064954 A1 | 3/2013 | Ochomogo et al. |
| 2013/0122071 A1 | 5/2013 | Cathala et al. |
| 2014/0134255 A1 | 5/2014 | Saito et al. |
| 2014/0161854 A1 | 6/2014 | Kotyla |
| 2014/0271877 A1 | 9/2014 | Wilmott |
| 2014/0272071 A1 | 9/2014 | Wilmott et al. |
| 2015/0313810 A1* | 11/2015 | Plismy Juquel ..... A61K 8/8158 424/78.03 |
| 2016/0213757 A1 | 7/2016 | Edelson et al. |
| 2016/0250111 A1 | 9/2016 | Wilmott et al. |
| 2020/0100518 A1 | 4/2020 | Wilmott et al. |

FOREIGN PATENT DOCUMENTS

| | | | | |
|---|---|---|---|---|
| CN | 1125145 | C | 10/2003 | |
| CN | 111629789 | A * | 9/2020 | ............ A61K 8/062 |
| EP | 0103910 | A1 * | 3/1984 | |
| EP | 2162120 | A2 | 3/2010 | |
| EP | 2 228 058 | A1 | 9/2010 | |
| JP | 2000-95634 | A | 4/2000 | |
| JP | 2000-95636 | A | 4/2000 | |
| JP | 2000-95638 | A | 4/2000 | |
| JP | 2002-142671 | A | 5/2002 | |
| JP | 2002-543263 | A | 12/2002 | |
| JP | 2004-501068 | A | 1/2004 | |
| JP | 2004-57042 | A | 2/2004 | |
| JP | 2004-346039 | A | 12/2004 | |
| JP | 2006-256971 | A | 9/2006 | |
| JP | 2007-117021 | A | 5/2007 | |
| JP | 2007-184542 | A | 7/2007 | |
| JP | 2007-238549 | A | 9/2007 | |
| JP | 2008-013470 | A | 1/2008 | |
| JP | 2009-518027 | A | 5/2009 | |
| JP | 2010-124817 | A | 6/2010 | |
| JP | 2013-49668 | A | 3/2013 | |
| WO | WO-0203916 | A2 * | 1/2002 | ............ A61K 8/062 |
| WO | 2002/34218 | A2 | 5/2002 | |
| WO | 2007/120500 | A2 | 10/2007 | |
| WO | WO-2009099546 | A2 * | 8/2009 | ............... A23L 2/52 |
| WO | 2013/018584 | A1 | 2/2013 | |

OTHER PUBLICATIONS

Flanagan et al.; "Microemulsions: A Potential Delivery System for Bioactives in Food"; Critical Rev. Food Sci Nutrition, vol. 46, pp. 221-237, 2006 Abstract; Figgure 2, Figure 6.

Williams, et al.; "Penetration Enhancers", Advanced Drug Delivery Reviews, vol. 64, 2012, pp. 128-137, available online Sep. 13, 2012.

Sakai, Toshio; "Surfactant-Free Emulsions", Current Opinion in Colloid & Interface Science, vol. 13, 2008, pp. 228-235.

ICI Americas Inc .; "The HLB System a Time-Saving Guide to Emulsifier Selection"; Revised Mar. 1980, pp. 1-22.

International Search Report dated Jan. 31, 2022 from corresponding International Patent Application No. PCT/US2021/056802, 3 pages.

Written Opinion dated Jan. 31, 2022 from corresponding International Patent Application No. PCT/US2021/056802. 4 pages.

Extended European Search Report dated Oct. 18, 2024 for European Application No. 21887417.0.

* cited by examiner

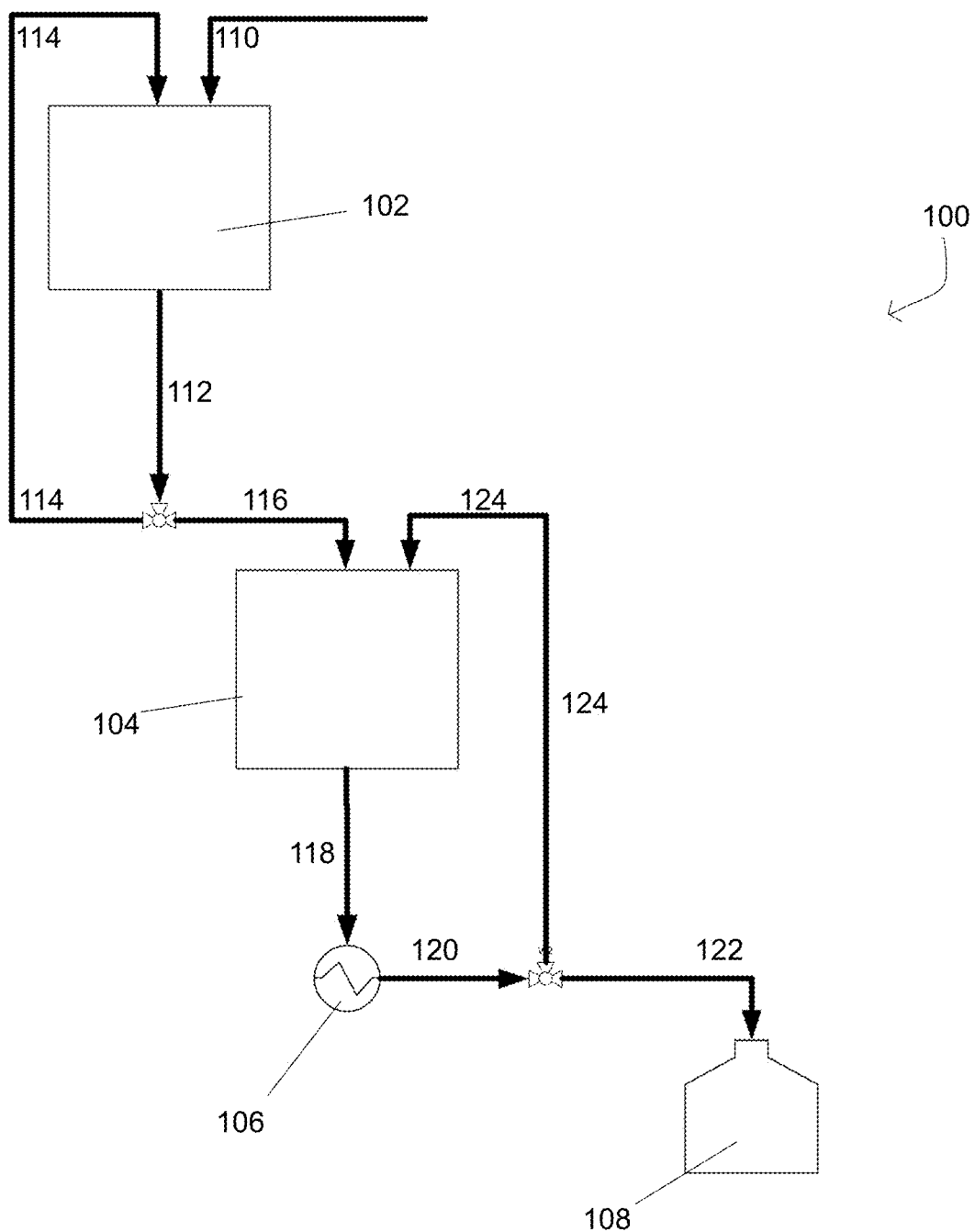

SYSTEM, METHOD, AND COMPOSITION FOR SKIN IMPROVEMENT AND TRANSIENT FLORA REDUCTION

CROSS REFERENCE TO RELATED APPLICATIONS

This application claims the benefit of U.S. Provisional Application Ser. No. 63/106,208, filed Oct. 27, 2020, the entire contents of which are incorporated by reference herein.

BACKGROUND

1. Field of the Disclosure

The present disclosure relates to compositions for improving skin condition and reducing the presence of transient flora on skin. More particularly, the present disclosure relates to such compositions that are topically applied and that have one or more stabilized hydrophobe-in-water, submicron dispersions dispersed therein.

2. Description of Related Art

Transient skin flora refers to the microorganisms that transiently colonize the superficial layers of the skin. These microorganisms include bacteria, fungi and/or viruses. Transient skin flora reaches the hands, for example, by direct skin-to-skin contact or indirectly via objects and other substrates.

Transient skin flora removal can be, for example, by routine hand washing with soap. In the absence of hand washing or during extended durations without hand washing, the amount of transient skin flora increases. Cross-contamination between humans can occur, for example, through contaminated hands.

The skin is composed of three layers, the epidermis, dermis and hypodermis, in order with epidermis being the outermost layer.

The most superficial layer of the epidermis is called the stratum corneum. The stratum corneum reduces water loss, provides protection against abrasion and microorganisms, and generally act as a permeability barrier to the environment. Renewal of the stratum corneum is controlled by complex regulatory systems of cellular differentiation.

Ethanol 60-95% v/v is an effective active agent for use in antiseptic hand hygiene or handwash product. However, use of high amounts of such a solvent can alter the stratum corneum by extracting skin lipids. These alterations can cause an increase of keratinocyte proliferation and differentiation as a response to restore the skin barrier. The increase perturbs the uptake of nutrients, such as essential fatty acids and the protein and lipid syntheses needed for skin barrier function. Such high amounts of solvent cause skin nutrients to be stripped or flashed off.

Without conventional surfactants, it is difficult to add hydrophobes to, for example, hand hygiene or handwash products because of the high levels of alcohol required to be effective at reducing transient flora. Simply adding hydrophobes to those compositions results in instability, for example, flocculation, Ostwald ripening, sedimentation, coalescence, creaming, or phase inversion. However, the surfactants that are commonly used in antiseptic hand hygiene or handwash products do not replenish nutrients that are stripped or flashed off. In fact, surfactants are known to irritate the skin and can have toxic effects on the skin.

SUMMARY

The present disclosure provides alcohol-containing compositions for topical application to the skin that reduce or inactivate transient skin flora and/or temporarily suppress the growth of transient skin flora and improving the condition of the skin.

The present disclosure provides such compositions for topical application to the skin and that reduce or inactivate transient skin flora and/or temporarily suppress the growth of transient skin flora that have a submicron dispersion while improving the condition of the skin.

The present disclosure further provides such compositions that have one or more stabilized hydrophobe-in-water, submicron dispersions dispersed that can serve as multifunctional delivery vehicles dispersed therein to transport conditioning agents onto and into the skin barrier.

The present disclosure further provides such compositions that are typically in but not limited to the form of a liquid, gel, spray or foam.

The present disclosure provides a method of preparing such compositions by multi-step homogenization, namely a low energy homogenization followed by a high energy homogenization.

The present disclosure provides a method of applying such compositions to a skin substrate.

The present disclosure further provides such compositions that counteract the negative effects of high alcohol concentration on skin and help restore balance in the skin barrier. For example, the compositions of the present disclosure, supply the skin with moisturization and replenishing natural fatty acids that are stripped away during the use of a high alcohol product.

BRIEF DESCRIPTION OF THE DRAWING

FIG. 1 is an example process diagram according to the present disclosure.

DETAILED DESCRIPTION OF THE DISCLOSURE

As used herein the term, alcohol generally refers to an organic compound that carries at least one hydroxyl functional group (—OH) bound to a saturated carbon atom. Examples include mono, di, tri, tetra or penta alcohols. Examples further include Ethanol or Isopropanol. Examples still further include methanol, ethanol, isopropanol, propanol, butanol, ethylene glycol, propylene glycol, butylene glycol, pentylene glycol, glycerol, tetritol, pentitol, 1,3 propane diol, and the like, or mixtures thereof.

An initial or base composition according to the present disclosure includes at least 50% wt/wt of one or more alcohols in the aqueous continuous phase. In examples, the base composition includes at least about 60%, at least about 62%, at least about 65% or at least 70% alcohols. Alcohols can be present in the base composition in a range of about 60%-95% alcohols. Volume/volume equivalents can be calculated as known in the art.

A dispersion as used herein means, a suspension of hydrophobic agent particles in an aqueous fluid or an aqueous-solvent fluid The compositions of the present disclosure contain one or more dispersions of submicron particles of a hydrophobic agent in an aqueous continuous phase. Such dispersions are referred to herein as hydrophobe-in-water dispersions. Oil-in-water dispersions are examples of hydrophobe-in-water dispersions. Hydrophobe-in-water dispersions can also have, for example, silicone or Omega-3-6-9 Fatty Acids as the hydrophobes dispersed in an aqueous continuous phase.

An "agent" as used in this application, is a substance that brings about a chemical or physical effect or causes a chemical reaction.

A "hydrophobe" or "hydrophobic agent," as used in this application, is a molecule or compound that is repelled by or has no attraction to water and hydrophobe has little or no solubility in water, for example less than 0.1%, less than 0.05%, or less than 0.03%. Examples include oils, alkanes, and esters of fatty acids.

Each dispersion can provide a multifunctional delivery vehicle for active ingredients or pre-biotics, including one or more: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, exfoliating agents, wound healing agents, sebum modulators, immunomodulators, hormones, botanicals, moisturizers, astringents, sensates, antibiotics, anesthetics, steroids, tissue healing substances, tissue regenerating substances, amino acids, peptides, minerals, ceramides, hyaluronic acids, skin bleaching ingredients, and any combinations of the foregoing. Advantageously, the dispersions provide such a multifunctional delivery vehicle without the need for conventional surfactants or heating which can alter or damage actives.

The one or more stable hydrophobe-in-water, submicron dispersions according to the present disclosure are prepared prior to being added to the initial or base composition. Surprisingly, the particles of the submicron dispersion instantly disperse in the aqueous continuous phase and remain stably dispersed.

The dispersions according to the present disclosure are essentially free of surfactants. Surfactants are compounds that lower the surface tension between two liquids. When there are sufficient amounts of surfactant molecules present in a solution they combine together to form structures called micelles. As the micelle forms, the surfactant heads position themselves so they are exposed to water, while the tails are grouped together in the center of the structure protected from water.

Surfactants are defined herein to be amphiphiles or amphiphilic compounds having a Critical Micelle Concentration (CMC) greater than $10^{-8}$ mol/L or micelle forming amphiphiles or amphiphilic compounds.

The dispersions according to the present disclosure can be free of amphiphilic compounds with a CMC greater than $10^{-8}$ mol/L.

The dispersions according to the present disclosure can have 25% by wt. of the hydrophobic phase of the dispersion or less amphiphiles or amphiphilic compounds having a CMC greater than $10^{-8}$ mol/L, preferably 20% by wt. or less, more preferably 15% or less, still more preferably 10% by wt. or less, and most preferably 4.9% by wt. or less. These amphiphiles or amphiphilic compounds are non-micelle forming and thus not surfactants.

In the dispersions according to the present disclosure, amphiphilic compounds with a CMC of $10^{-8}$ mol/L or lower can be present in the dispersion in an amount of at most 10%, at most 4.97%, preferably at most 3.15%, more preferably at most 1.5%, and most preferably at most 0.95% by wt. of the dispersion. In still other examples, the amphiphilic compounds with a CMC of $10^{-8}$ mol/L or lower comprise at most 0.89% or 0.79% of the dispersion.

Without wishing to be bound by a single theory, it is believed that the mechanical processing imparts the stability. The dispersions offer manufacturing flexibility because the processing makes them compatible with a wide variety of base compositions, unlike conventional emulsions that require specifically tailored processing and require non-mechanical processing, such as chemical or heating.

The dispersions used in the composition of the present disclosure are produced by a mechanical process that imparts a small and substantially homogeneous submicron particle size to each particle of a hydrophobic agent.

A dispersion of one or more hydrophobic agent(s) used in the present disclosure possesses a net negative charge after mechanical processing, such as by high-pressure high-shear processing.

In examples, the net negative charge is −30 mV or lower. In other examples, my, the net negative charge is −32 mV or lower. In yet other examples, my, the net negative charge is −35 mV or lower Preferred methods of mechanical processing impart a slight repulsive force that causes the particles of the one or more hydrophobic agent(s) to repel or move away from each other in the dispersion, thus enhancing the stability and dispersibility of the dispersion.

The compositions and dispersions are mechanically processed under temperature conditions different from traditional emulsions that require heat. In addition to surfactants, traditional emulsions typically also require temperatures of 70-120° C. Preparation of these traditional emulsions further require an activation energy to be achieved in addition to mechanical energy.

The compositions and dispersions are prepared under ambient temperatures. Processing can be below 50° C., below 45° C., below 40° C. and below 30° C. Advantageously, compositions and dispersions of the present disclosure require only mechanical energy to be formed.

Moreover, the amount of heat required for traditional emulsion preparation is unsafe for preparing compositions according to the present disclosure because of the high level of alcohol content. Alcohols have a low flashpoint and are flammable at high concentrations. For example, above about 11° C. to 15° C. ethanol or isopropanol can emanate vapors in a quantity sufficient to form an ignitable mixture with the air.

The dispersion used in the composition of the present disclosure can be mechanically processed until most or all particles of the hydrophobic agent(s) are sufficiently small and essentially monodispersed to be on the side of a dispersity barrier, where a sufficient quantity of the particles are at their smallest size (critical or terminal particle size) to minimize the risk of sedimentation or creaming, and to make the dispersion stable for commercial applications.

The dispersity barrier is a different value for each hydrophobic agent and depends on the physical and chemical properties of the hydrophobic agent. The particles also possess a net negative charge which repulse one another. The stability of the dispersion and the diffusion of the hydrophobic agent(s) throughout the aqueous continuous phase are further enhanced when a sufficient number of particles exceed the electrostatic barrier where the magnitude of the charge creates a force of repulsion that is greater than the force on the particles to coalesce. The more particles of hydrophobic agent that exceed both the dispersity barrier and the electrostatic barrier, the greater the stability of the dispersion.

As discussed above, the dispersions of the present disclosure can be produced by high-pressure high-shear homogenization. It has been unexpectedly found by the present disclosure that the initial particle size prior to high-pressure high-shear homogenization is, in part, critical to achieving the stability of the combined continuous phase with the dispersions.

Each material has a terminal particle size achievable by high-pressure high-shear homogenization. The terminal particle size varies based on the material. Surfactant processes yield a different terminal particle size and with undesirable chemical additives.

In an exemplary embodiment, prior to high-pressure high-shear homogenization to create the dispersions of the present disclosure, an initial average particle size of the raw material components for the dispersion is on the order of several microns.

After high-pressure high-shear homogenization, prior to combining with the initial or base composition, an average particle size of the components of the dispersion can be, about 200 nm, about 205 nm, about 210 nm, about 215 nm, about 220 nm, about 225 nm, about 250 nm, about 275 nm, about 300 nm, about 325 nm, about 350 nm, about 375 nm, about 400 nm, about 425 nm, about 450 nm, about 475 nm, about 480 nm, about 500 nm, about 525 nm, about 550 nm, about 575 nm, 600 nm, about 625 nm, about 650 nm, about 675 nm, about 700 nm, about 725 nm, about 750 nm, and any ranges or subranges between any of the foregoing and including endpoints.

Referring to FIG. 1, in an example, the dispersions can be created by a dispersion process 100 that uses a multi-step homogenization, namely a low energy homogenization followed by a high energy homogenization.

The components for the dispersion are feed into a homogenizer 102 via an input stream 110, homogenizing, and outputting via an outlet stream 112.

Homogenizer 102 is a low energy homogenizer.

Nonlimiting examples include mixing, rotor stator, vacuum homogenization, media mills, and colloid mills.

In examples, a mixture of water, a humectant, and one or more hydrophobes are low energy homogenized until an average particle size of the hydrophobes in the mixture is less than 150 microns to yield an outflow.

Homogenization by homogenizer 102 is mechanical and is performed at ambient pressure and temperature.

Homogenization is performed until an average particle size of the hydrophobes in the mixture is less than 150 microns, less than 100 microns, less than 80 microns, less than 50 microns, less than 40 microns, less than 30 microns, less than 25 microns, preferably less than 20 microns, more preferably less than 12 microns, still more preferably less than 10 microns, and most preferably less than 8 microns. Surprisingly, such low energy mechanical homogenization prior to high-pressure high-shear processing achieves optimal hydrophobe-in-water dispersions.

Optionally, stream 112 can be recycled as stream 114 and recombined with input stream 110.

Stream 112 is output from homogenizer 102 and the outflow is fed into a second, homogenizer, Apparatus 104, as stream 116.

Apparatus 104 is a high energy homogenizer.

Non-limiting examples of homogenizer 104 include high-pressure and high-shear devices, high-pressure homogenizers, microfluidizers, or sonication.

After high-pressure high-shear processing in apparatus 104, a heat exchanger 106 removes heat from stream 118 and outputs a stream 120.

Stream 120 is collected as stream 122 in a vessel 108.

Optionally, stream 120 can be refed into high-pressure high-shear apparatus 104 as stream 124 for further high-pressure high-shear processing.

Heat exchanger 106 maintains temperatures in apparatus 104 below 35 C°, preferably below 32 C°, more preferably below 29 C°, and most preferably below 27 C°.

The pressure in apparatus 104 can be from about 6,000 to about 31,000 psi, preferably from about 11,000 to about 24,000 psi, and more preferably from about 13,000 to about 19,000 psi. Surprisingly, throughput decreases as pressure increases.

In examples, apparatus 104 causes two or more particle streams to collide with each other, under pressure, thereby reducing the size of the particles.

In another example the dispersions are produced by a combination of shear forces, impact forces, and energy dissipation forces.

Shear forces are unaligned forces that pushing a portion of the particle body in one specific direction, and another portion the particle body in the opposite direction. Thereby, the particles are caused to fracture and be broken up into smaller particles.

Impact forces occur when two particles collide with each other or with another object/body and are the result of inelastic collisions. High velocity collisions between the particles cause the particles to exhibit a brittle behavior causing them to fracture and be broken up into smaller particles.

Dissipation forces increase the entropy of the system. Viscous forces, for example are the force that act on the particles in the direction in which the particles are moving relative to other particles and hence opposite to the direction in which the particles are moving relative to each other.

In an exemplary embodiment, dispersion process 100 will produce a dispersion of submicron particles of the one or more hydrophobic agent(s) in which at least 79 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 79 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 85 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 85 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 87 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 87 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 90 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 90 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 93 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 93 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 95 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 95 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

In exemplary embodiments, dispersion process 100 of the present disclosure will produce a suspension of submicron particles of the one or more hydrophobic agent(s) in which at least 98 wt % of the total particles in the dispersion are ±200 nm of the value for the average particle size, more preferably are ±150 nm, and still more preferably are ±125 nm, ±100 nm, and ±75 nm, respectively, of the value for the average particle size.

In exemplary embodiments, at least 98 wt % of the total particles in the dispersion are ±1.50 standard deviations of the value for the average particle size, more preferably are ±1.20 standard deviations of the value for the average particle size, and most preferably are ±1.00 standard deviation of the value for the average particle size.

Dispersion process 100 according to the present disclosure imparts a net negative charge on the particles of the dispersion. Preferably the net negative charge is −30 mV or lower, more preferably −32 mV or lower, and most preferably −35 mV or lower.

The particles of the dispersions of the present disclosure have a net negative charge so that the particles exhibit an anti-coalescent tendency. Each particle is acted upon by a repulsive force from each surrounding particle in a 3-dimensional space or volume such as the base or initial composition.

The portion (or alternatively, the ratio) of particles that are "over" the electrostatic barrier (i.e. the point at which repulsion forces exceed the coalescing forces in the dispersion), in relation to the total number of particles, is a measure of the stability and quality of the dispersion. The electrostatic barrier has a different value for each hydrophobic agent and depends on the physical and chemical properties of the hydrophobic agent. However, the value of the electrostatic barrier for hydrophobic agents can fall within the same range. In addition, in some instances the value of the electrostatic barrier for a hydrophobic agent can be moved somewhat by the selection of processing conditions.

In an exemplary embodiment, at least 20 wt % of the total particles in the dispersion are over the electrostatic barrier (meaning that repulsion forces exceed coalescing forces for 20 wt % of the particles), indicating that the dispersion is stable. In another preferred embodiment, 50 wt % or more of the particles are over the electrostatic barrier, indicating that the dispersion is more stable relative to the earlier embodiment. In a preferred embodiment, 75 wt % or more of the particles are over the electrostatic barrier, indicating that the dispersion is even more stable. In increasingly preferred embodiments, 87 wt % or more, 90 wt % or more, 95 wt % or more, and 97 wt % or more of the particles of the hydrophobic agent are over the electrostatic barrier, respectively, indicating dispersions that are increasingly stable.

The particle sizes in the dispersions according to the present disclosure are maintained above 100 nm by dispersion process 100 so that the average particle size is greater than 100 nm, preferably 120 nm.

Dispersions having an average particle size that is greater than 100 nm have the additional benefit of being regulatory compliant with guidelines that define nanotechnology as particles with an average particle size of less than 100 nm, i.e. that are smaller than the low end of the particle size range of the present disclosure.

The dispersions of the present disclosure containing submicron particles of one or more hydrophobic agent can be stored in a concentrated form prior to use, such as about 30 wt % to about 70 wt %. Advantageously, the concentrated dispersion can be diluted nearer to the time when it is added to the base or initial composition. For example, the concentrate can be diluted 1.5-fold, 2-fold, 5-fold, 10-fold, 50-fold, 100-fold, 200-fold, and even 1000-fold.

Dilution of the concentrate to the desired concentration can be used to optimize the benefits of the dispersion to skin.

Advantageously, the first (or second, third etc.) dispersion can be diluted to a desired concentration without upsetting stability, namely without causing flocculation, Ostwald ripening, sedimentation, coalescence, creaming, and phase inversion.

The method can also include preparing a second dispersion. The second submicron dispersion can be mixed into the first submicron dispersion prior adding to the base or initial composition. Alternatively, the first and second dispersions can be added directly to the base or initial composition.

Advantageously, the first (or second, third etc.) dispersion can be mixed in various ratios without upsetting stability, namely without causing flocculation, Ostwald ripening, sedimentation, coalescence, creaming, and phase inversion.

Subjecting the mixture of components to be dispersed to one or more preparatory steps, such as homogenizing in homogenizer 102, can facilitate increasing the number of elastic collisions in the apparatus 104 so that the particles of the hydrophobic agent are approximately the same size and mass before high-pressure high-shearing, and their elastic collision produces particles that that are smaller but remain approximately equal to each other in size and mass. The resulting particles are then analyzed for particle size, degree of monodispersity, and magnitude of the electrostatic charge. The desired properties of the particles in the dispersion are thus attained more quickly, and with less fuel, less energy, and less cost than conventional techniques, and so manufacturing is more commercially viable.

The hydrophobic agent can be colorants, such as for example annatto oil, paprika oil, chlorphyll, lycopene, carotenoids. xanthophylls or the like. The hydrophobic agents can be essential nutrients, such as for example, vitamins such as Vitamin D and its derivatives, Vitamin A and its derivatives, Vitamin E and its derivatives, Vitamin K, Vitamin F, Vitamin P, and the like. Other such nutrients include for example lipoic acid, lycopene, ceram ides, ubiqinone, sterols, flavonoids, cholesterol, sphingolipids, prostaglandins, docosahexaenoic acid, and the like.

The hydrophobic agents can be fragrances, such as for example terpenes, isoterpenenes, alkyl lactones, essential oils, natural oils such as vanilla, and the like. The hydrophobic agents can be aroma providers that impart aroma to or modify aroma of a topical composition.

The hydrophobic agents in the dispersions can be present in an amount of about 0.01% wt. to about 50%, or about 5% to about 30%, or about 10% to about 25%, by wt.

It is the small size of the dispersion particles that imparts stability. The small size minimizes the tendency of hydrophobic particles to coalesce. The commercially viable stability described above, namely at least 180 days allows a useful amount of time in which to store topical compositions to maintain product integrity.

The stability is further manifested in that two or more distinct dispersions can be mixed without decreasing the stability of the various component hydrophobic agent particles, or a dispersion can be diluted into aqueous fluid or aqueous-solvent fluid without decreasing the stability of the component hydrophobic agent particles.

Further, if hydrophobic agent A were not compatible with hydrophobic agent B when mixed, nonetheless a dispersion of the invention of hydrophobic agent A can be mixed with a dispersion of hydrophobic B, since the individual particles maintain their integrity.

Silicone oil and olive oil exemplify such incompatible hydrophobic agents.

A commercially viable period of time according to the present disclosure can be 28 days, one month, two months, and three months and ranges therebetween.

Emulsion stability is dependent on a variety of parameters such as the zeta potential, particle size, crystal formation, and water binding activity of the ingredients employed to achieve the desired rheological properties of the product. These parameters are dependent on the temperature to which the oil and water phases are heated, the rate of heating, the method and rate of mixing of the phases when combined at elevated temperatures, and the rate of cooling. Most emulsions require heating to ensure that all higher melting point materials, such as waxes and butters, are completely melted, dissolved, or dispersed in the appropriate phase.

If any one of the processing variables is modified unexpectedly, particle size variations may occur or the crystalline properties of the emulsion can be compromised.

The presence of a significant amount of surfactant in an emulsion can strip the lipid barrier of the skin. It can also disrupt the lipid bilayer of epithelial cell membranes, thereby leaving the tissue vulnerable. The surfactants themselves may evoke an irritation. Furthermore, the resulting damaged skin barrier then can permit the passage of other materials that can cause irritation or increase skin sensitivity. Advantageously, the composition of the present disclosure does not require surfactants for stability.

As discussed above, each dispersion can provide a multifunctional delivery vehicle for active ingredients or prebiotics, including one or more: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, antibacterial agents, antiviral agents, antiaging agents, photoprotection agents, exfoliating agents, wound healing agents, sebum modulators, immunomodulators, hormones, botanicals, moisturizers, astringents, sensates, antibiotics, anesthetics, steroids, tissue healing substances, tissue regenerating substances, amino acids, peptides, minerals, ceram ides, hyaluronic acids, skin bleaching ingredients, and any combinations of the forgoing.

Anti-acne agents include, but are not limited to, salicylic acid, retinoic acid, alpha hydroxy acid, benzoyl peroxide, sodium sulfacetamide, clindamycin, hydrocortisone, tetrahydrozoline, and mixtures thereof.

Antimicrobial agents include, but are not limited to, Benzalkonium chloride, Benzethonium chloride, Chlorhexidine gluconate, Chloroxylenol, Clindamycin, Cloflucarban, erythromycin, Fluorosalan, Hexachlorophene, Hexylresorcinol, Iodine complex, Iodine tincture, Para-chloromercuriphenol, Phenylmercuric nitrate, Thimerosal, Vitromersol, Zyloxin, Triclocarban, Triclosan, Methyl-benzethonium chloride, Nonyl phenoxypoly (ethyleneoxy) ethanol-iodine, Para-chloro-meta-xylenol, Providone-iodine complex, Poloxamer-iodine complex, Undecoylium chloride-iodine complex, and any combinations of the foregoing.

Anti-inflammatory agents include, but are not limited to, Alidoxa, Allantoin, Aloe Vera, Aluminum acetate, Aluminum hydroxide, Bismuth subnitrate, Boric acid, Calamine, Casein, microporous cellulose, Cholecalciferol, Cocoa butter, Cod liver oil, Colloidal oatmeal, Cysteine hydrochloride, Dexpanthenol, Dimethicone, Glycerin, alpha-bisabolol, sea whip extract, glycyrrhetinic acid and its salts and derivatives, Kaolin, Lanolin, Live yeast cell derivative, Mineral oil, Peruvian balsam, Petrolatum, Protein hydrolysate, Racemethionine, Shark liver oil, Sodium bicarbonate, Sulfur, Talc, Tannic acid, Topical starch, Vitamin A, Vitamin E, White petrolatum, Zinc acetate, Zinc carbonate, Zinc oxide, Hydrocortisone, Betamethasone, Ibuprofen, Indomethacin, Acetylsalicylic acid, Tacrolimus, Fluocinolone acetonide, Sodium sulfacetamide, and any combinations of the foregoing.

Analgesics include, but are not limited to, diphenhydramine, tripelennamine, benzocaine, dibucaine, lidocaine, tetracaine, camphor, menthol, phenol, resorcinol, matacresol, juniper tar, methylsalicylate, turpentine oil, capsicum, methyl nicotinate, beta-glucan, and any combinations of the foregoing.

Anti-erythemal agents include, but are not limited to, tetrahydrozoline and hydrocortisone, and any combinations of the foregoing.

Antipruritic agents include, but are not limited to, diphenhydramine, pramoxine, antihistamines, and any combinations of the foregoing.

Anti-edema agents include, but are not limited to, pregnenolone acetate, tannin glycosides, and any combinations of the foregoing.

Anti-psoriatic agents include, but are not limited to, calcipotriene, coal tar, anthralin, Vitamin A, hydrocortisone, retinoic acid, alpha hydroxy acid, dovonex, salicylic acid, sunscreen agents, indomethacin, urea; anthralin, and any combinations of the foregoing.

Antifungal agents include, but are not limited to, clioquinol, haloprogin, miconazole nitrate, clotrimazole, metronidazole, tolnaftate, undecylenic acid, iodoquinol, and any combinations of the foregoing.

Skin protectants include, but are not limited to, cocoa butter, dimethicone, petrolatum, white petrolatum, glycerin, shark liver oil, allantoin, and any combinations of the foregoing.

Sunscreen agents include, but are not limited to, ethylhexyl methoxycinnamate, avobenzone, benzophenones, octocrylene, ethylhexyl salicylate, homomethyl salicylate, triethanolamine salicylate, menthyl anthranilate, PABA, octyl dimethyl PABA, 2-ethoxyethyl p-methoxycinnamate, phenylbenzimidazole sulfonic acid, titanium dioxide, zinc oxide, and any combinations of the foregoing.

Antioxidants include, but are not limited to, scavengers for lipid free radicals and peroxyl radicals, quenching agents, astaxanthin, tocopherol, butylated hydroxytoluene (BHT), beta carotene, Vitamin A, ascorbic acid and aliphatic derivatives, ubiquinol, ferulic acid, azelaic acid, thymol, catechin, sinapic acid, ethylenediaminetetraacetic acid (EDTA), lactoferrin, rosmariquinone, hydroxytyrosol, sesamol, 2-thioxanthine, nausin, malvin, carvacone, chalcones, glutathione isopropyl ester and other aliphatic derivatives, xanthine, melanin, guanisone, loporphyrins, 8-hydroxyxanthine, 2-thioxanthione, Vitamin B12, plant alkaloids, catalase, quercetin, tyrosine, superoxide dismutase (SOD), cysteine, methionine, genistein, nordihydroguaiaretic acid (NDGA), procyanidin, hamamelitannin, ubiquinone, trolox, licorice extract, propyl gallate, and any combinations of the foregoing.

Vitamins include, but are not limited to, Vitamin E, Vitamin A palmitate, Vitamin D, Vitamin F, Vitamin B6, Vitamin B3, Vitamin B12, Vitamin C, ascorbyl palmitate, Vitamin E acetate, biotin, niacin, dl-panthenol, and any combinations of the foregoing.

Material and thus particle size variations can yield different textures by simply adding to the base dispersion, for example, texturizing modifiers, like wax, stearic acid, and stearyl alcohols.

The present compositions can be formulated for dispensing and application to the skin as a gel, cream, light liquid, heavy liquid, or mist.

Optionally, in certain embodiments, one or more rheological modifying agents can be included in the base composition. Such rheological modifying agent can be present in the base composition in an amount from about 0.01% wt to about 10.00% wt, preferably about 0.10% wt to about 5.00% wt, and more preferably from about 0.20% wt to about 2.00% wt.

Rheological modifying agents can be included in the base composition or in the dispersion.

In certain embodiments, one or more rheological modifying agents can be included in the dispersion. Such rheological modifying agent can be present in the dispersion in an amount from about 0.01% wt to about 10.00% wt, preferably about 0.10% wt to about 5.00% wt, and more preferably from about 0.20% wt to about 2.00% wt.

Suitable rheological modifying agents include, but are not limited to, phosphorylated starch derivative, carbohydrate based rheological modifying agents, polymeric and copolymeric rheological modifying agents, inorganic rheological modifying agents, protein rheological modifying agents, polypeptide rheological modifying agents, and any combinations of the foregoing.

Examples of a phosphorylated starch derivative include, but are not limited to, starches containing a phosphate group. Suitable phosphorylated starch derivatives include, but are not limited to, hydroxyalkyl starch phosphates, hydroxyalkyl distarch phosphates, and any combination of any of the foregoing. Non-limiting examples of hydroxyalkyl starch phosphates and hydroxyalkyl distarch phosphates include: hydroxyethyl starch phosphate, hydroxypropyl starch phosphate, hydroxypropyl distarch phosphate (including sodium hydroxypropyl starch phosphate), and any combinations of the foregoing.

Non-limiting examples of suitable carbohydrate based rheological modifying agents include algin and derivatives and salts thereof (such as algin, calcium alginate, propylene glycol alginate, and ammonium alginate); carrageenan (Chondrus *crispus*) and derivatives and salts thereof (such as calcium carrageenan and sodium carrageenan); agar; cellulose and derivatives thereof (such as carboxymethyl hydroxyethylcellulose, cellulose gum, hydroxyethylcellulose, hydroxypropylcellulose, hydroxypropyl methylcellulose, and ethylcellulose); chitosan and derivatives and salts thereof (such as hydroxypropyl chitosan, carboxymethyl chitosan, and chitin); gellan gum; guar (*Cyamopsis tetragonoloba*) and derivatives thereof (such as guar hydroxypropyltrimonium chloride and hydroxypropyl guar); hyaluronic acid and derivatives thereof (such as sodium hyaluronate); dextran and derivatives thereof; dextrin; locust bean (*Ceratonia siliqua*) gum; starches (such as starch polyacrylonitrile copolymer-potassium salt and starch polyacrylonitrile copolymer-sodium salt); pectin; *sclerotium* gum; tragacanth (*Astragalus* gummifer) gum; xanthan gum and derivatives thereof; and any combinations of the foregoing.

Non-limiting examples of suitable polymeric and copolymeric rheological modifying agents include acrylates, methacrylates, polyethylene and derivatives thereof, and any combination of any of the foregoing. Suitable acrylates and methacrylates include, but are not limited to, carbomer and derivatives and salts thereof, acrylates/C10-C30 alkyl acrylate crosspolymer, acrylates/ceteth-20 itaconate copolymer, acrylates/ceteth-methacrylate copolymers, acrylates/steareth-methacrylate copolymers, acrylates/steareth-20 itaconate copolymers, acrylates/steareth-50 acrylate copolymers, acrylatesNA crosspolymers, acrylates/vinyl isodecanoate crosspolymers, acrylic acid/acrylonitrogen copolymers, ammonium acrylates/acrylonitrogen copolymers, glyceryl polymethacrylate, polyacrylic acid, PVM/MA decadiene crosspolymer, sodium acrylate/vinyl isodecanoate crosspolymers, sodium carbomer, ethylene/acrylic acid copolymer, ethyleneNA copolymer, acrylates/acrylamide copolymer, acrylate copolymers, acrylates/hydroxyester acrylate copolymers, acrylate/octylarylamide copolymers, acrylates/PVP copolymers, AMP/acrylate copolymers, butylester of PVM-MA copolymer, carboxylate vinyl acetate terpolymers, diglycol/CHDM/isophthalates/SIP copolymer, ethyl ester of PVM-MA copolymer, isopropyl ester of PVM-MA copolymer, octylacrylamide/acrylate/butylaminoethyl methacrylate copolymers, polymethacrylamidopropyltrimonium chloride, propylene glycol oligosuccinate, polyvinylcaprolactam, PVP, PVP/dimethylaminoethylmethacrylate copolymer, PVP/DMAPA acrylate copolymers, PVP/carbamyl polyglycol ester, PVPNA copolymer, PVPNA vinyl propionate copolymer, PVP/vinylcaprolactam/DMAPA acrylate copolymers, sodium polyacrylate, VA/butyl maleate/isobornyl acrylate copolymers, VA/crotonates copolymer, VA/crotonates vinyl neodecanoate copolymer, VA/crotonates/vinyl propionate copolymer, vinyl caprolactam/PVP/dimethylaminoethylmethacrylate copolymer, hydroxyethyl Acrylate/Sodium Acryloyldimethy Taurate Copolymer, and any combinations of the foregoing.

Non-limiting examples of suitable inorganic rheological modifying agents include clays and derivatives thereof, silicates, silicas and derivatives thereof, and any combination of any of the foregoing. Suitable clays and derivatives thereof include, but are not limited to, bentonite and derivatives thereof, such as quaternium-18 bentonite; hectorite and derivatives thereof, such as quaterniums; montmorillonite; and any combinations of the foregoing. Suitable silicates include, but are not limited to, magnesium aluminum silicate, sodium magnesium silicate, lithium magnesium silicate, tromethamine magnesium aluminum silicate, and any combinations of the foregoing. Suitable silicas and derivatives thereof include, but are not limited to, hydrated silica, hydrophobic silica, spherical silica, and any combinations of the foregoing.

Suitable protein and polypeptide rheological modifying agents include, but are not limited to, proteins and derivatives and salts thereof, polypeptides and derivatives and salts thereof, and any combination of any of the foregoing. Non-limiting examples of protein and polypeptide rheological modifying agents include albumin, gelatin, keratin and derivatives thereof, fish protein and derivatives thereof, milk protein and derivatives thereof, wheat protein and derivatives thereof, soy protein and derivatives thereof, elastin and derivatives thereof, silk protein and derivatives thereof, and any combinations of the foregoing.

Particularly suitable rheological modifying agents include, but are not limited to, carbomer, acrylate/alkyl acrylate crosspolymers, acrylate/vinyl isododecanoate crosspolymer, xanthan gum, hydroxyethyl cellulose, locust bean gum, guar gum, and any combination of any of the foregoing. A suitable combination of rheological modifying agents comprises carbomer and an acrylate/alkyl acrylate copolymer, such as an acrylates/C10-C30 alkyl acrylate crosspolymer. According to the International Cosmetic Ingredient Dictionary and Handbook (7th ed., The Cosmetic, Toiletry, and Fragrance Association), carbomer is a homopolymer of acrylic acid crosslinked with an allyl ether of pentaerythritol, an allyl ether of sucrose, or an allyl ether of propylene. The term "acrylate/alkyl acrylate crosspolymer" includes, but is not limited to, copolymers of alkyl acrylates with one or more monomers of acrylic acid, methacrylic acid, or one of their short chain (i.e. C1-4 alcohol) esters, wherein the crosslinking agent is, for example, an allyl ether of sucrose or pentaerytritol. Preferably, the alkyl acrylates are C10-C30 alkyl acrylates. Examples of such copolymers include, but are not limited to, those commercially available as Ultrez-21, Ultrez-20, Carbopol™ 1342, Carbopol™ 1382, Pemulen™ TR-1, and Pemulen™ TR-2, from Novion, Cleveland, Ohio. Particularly suitable rheological modifying agents include, but are not limited to, hydrophilic gelling agents, such as carboxyvinyl polymers (carbomer), acrylic copolymers (e.g., acrylate/alkyl acrylate copolymers), polyacrylamides, Hydroxyethyl Acrylate/Sodium Acryloyldimethyl Taurate Copolymers, polysaccharides (e.g. hydroxypropylcellulose), natural gums (e.g., xanthan gum), clays, and any combinations of the foregoing.

Examples of fatty acids providing fatty acyl components, or which provide hydrophobic agents include, without limitation, for example: Butyric acid, Caproic Acid, Caprylic Acid, Capric Acid, Lauric Acid, Myristic Acid, Palmitic Acid, Palmitoleic Acid, Stearic Acid, Oleic Acid, Ricinoleic acid, Vaccenic Acid, Linoleic Acid, Alpha-Linolenic Acid (ALA), Gamma-Linolenic Acid (GLA), Arachidic Acid, Gadoleic Acid, Arachidonic Acid (AA), EPA, Behenic acid, Erucic acid, DHA, and Lignoceric acid.

Fatty acyl compositions of some oils useful in the invention, include without limitation: Almond Oil, Beef Tallow, Butterfat (cow), Butterfat (goat), Butterfat (human), Canola Oil, Cocoa Butter, Cod Liver Oil, Coconut Oil, Corn Oil (Maize Oil), Cottonseed Oil, Flaxseed Oil, Grape seed Oil, Illipe, Lard (Pork fat), Olive Oil, Palm oil, Palm Olein, Palm Kernel Oil, Peanut Oil, Safflower Oil, Sesame Oil, Shea nut, soybean Oil, Sunflower Oil, Walnut Oil.

Humectants are materials that bind water through hydrogen bonding. Humectants generally have multiple hydroxyl groups or amino groups. Mono, di, and poly carbohydrate or reduced carbohydrate molecules are particularly good humectants. Three-carbon trihydroxy compounds like glycerin are also particularly good.

Most 5 carbon and 6 carbon mono-, di, and poly saccharide will bind water. Glucose, ribose, fructose, xylose, xylitol, mannitol, and sucrose will bind water which is released into dry skin to improve its functionality. Polysaccharides composed of a long-chain of either a mono-carbohydrate, di carbohydrates, or poly-carbohydrates are also suitable humectants. Glycogen, hyaluronic acid, honey, and chondroitin sulfate are examples of Poly carbohydrates that can complex copious amount of water. They release moisture into the skin to keep it hydrated and supple for extended periods. Other examples of humectants are proteins, amino acids, and ammonium lactate. The aforementioned humectants are exemplary and not intended to be limiting.

EXAMPLES

Example 1: Moisturizing Hand Sanitizer

An example composition formulated as a moisturizing hand sanitizer was prepared and is summarized in Table 1.

The composition was prepared in three discrete parts that were later combined, namely phases, A-C.

In a first vessel, Phase A was prepared. Butylated hydroxytoluene (BHT) was mixed with Ethyl Alcohol until dissolved. Hand sanitizer concentrate (99% isopropanol) and Fragrance were added and mixed with a propeller until dissolved and uniform.

In a second vessel, Phase B was prepared. Glycerin, Butylene Glycol and Water were added and mixed until uniform. Phase B functions as a humectant.

In a third vessel, Phase C was prepared. O & R Dispersion BA NSB LP, LEI Modifier 200 HL BA NSB LP, and Spherica P-1500 (a texturizing agent) were added and mixed until uniform.

O & R Dispersion BA NSB LP includes Water, Glycerin, Preservative, Olive Oil, Echium Seed Oil, Hydrogenated Lecithin and Xanthan Gum.

LEI Modifier 200 HL BA NSB LP includes Water, Glycerin, Preservative, Dimethicone, Hydrogenated Lecithin and Xanthan Gum.

Spheron P-1500 is a high-performing, silica micro bead with improved stability. It has a wide array of benefits, including enhanced soft focus, increased slip and spreadability, moderate moisture/sebum absorption, and reduced oily feel and tack. Oil absorption 60 mL/100-gram powder Spheron P-1500 has an average particle size of 5 µm.

Phases A & B were combined and mixed until uniform.

Phase C was combined with Phases A & B and mixed until uniform.

Anchor mixing was performed to mix out any entrapped air, as necessary.

The composition of Example 1 had a pH of 6.23 and specific gravity of 0.906.

TABLE 1

Moisturizing Hand Sanitizer of Example 1

| Phase | Raw Material | Example 1A % | Example 1A Actual (g) | Example 1B % | Example 1B Actual (g) |
|---|---|---|---|---|---|
| A | Ethyl Alcohol (SDA 40-B 190 | 39.740% | 119.22 | 39.740% | 119.22 |
| A | Fresh Fragrance For Serum (Intarome #F-142673) | 0.400% | 1.20 | 0.400% | 1.20 |
| A | Hand Sanitizer Concentrate | 25.000% | 75.00 | 25.000% | 75.00 |
| A | BHT | 0.050% | 0.15 | 0.050% | 0.15 |
| B | Glycerin | 5.000% | 15.00 | 5.000% | 15.00 |
| B | Butylene Glycol | 0.000% | 0.00 | 3.000% | 9.00 |
| B | Water | 23.810% | 71.43 | 6.810% | 20.43 |
| C | O & R Dispersion BA NSB LP | 3.000% | 9.00 | 10.000% | 30.00 |
| C | LEI Modifier 200 HL BA NSB LP | 2.000% | 6.00 | 10.000% | 30.00 |
| C | Spherica P-1500 | 1.000% | 3.00 | 0.000% | 0.00 |
| | | 100.00% | 300.00 | 100.00% | 300.00 |

Example 2: Moisturizing Hand Sanitizer

Another example composition formulated as a moisturizing hand sanitizer was prepared and is summarized in Table 2.

Like in Example 1, the composition was prepared in discrete parts that were later combined. In this example, there are five parts or phases, namely phases, A-E.

In a first vessel, Phase A was prepared. Butylated hydroxytoluene (BHT) was mixed with Ethyl Alcohol until dissolved. Ultrez 20A and Fragrance were then added and mixed with a propeller until dissolved and uniform.

Ultrez 20A is a white powder, hydrophobically-modified crosslinked acrylate copolymer.

In a second vessel, Phase B was prepared. Glycerin, Butylene Glycol and Water were combined and mixed until uniform. Phase B functions as a humectant.

In a third vessel, Phase C was prepared. O & R Dispersion BA NSB LP and LEI Modifier 200 HL BA NSB LP were added and mixed until uniform.

Phases A, B, and C were combined and mixed until uniform.

Phase D, TRIS Amino or 2-amino-2-hydroxymethyl-1,3-propanediol, was added to neutralize to a pH of 6.0-7.0.

Phase E, Aminat G, was then added and mixed until uniform. AMINAT G® is based on a 20% solution of Na-Lauroyl-L-arginine ethyl ester monohydrochloride, hereinafter LAE®, in glycerin. LAE® is a unique antimicrobial active ingredient with cationic surfactant properties derived from natural occurring substances, L-arginine and lauric acid.

Anchor mixing was performed to mix out any entrapped air, as necessary.

TABLE 2

Moisturizing Hand Sanitizer of Example 2

| Phase | Raw Material | Example 2A % | Example 2A Actual (g) | Example 2B % | Example 2B Actual (g) | Example 2C % | Example 2C Actual (g) |
|---|---|---|---|---|---|---|---|
| A | SDA 40-B 190 | 60.800% | 364.80 | 60.800% | 364.80 | 65.800% | 394.80 |
| A | Fresh Fragrance For Serum (Intarome #F-142673) | 0.400% | 2.40 | 0.400% | 2.40 | 0.400% | 2.40 |
| A | Ultrez 20A | 0.500% | 3.00 | 0.500% | 3.00 | 0.500% | 3.00 |
| A | BHT | 0.050% | 0.30 | 0.050% | 0.30 | 0.050% | 0.30 |
| B | Glycerin | 5.000% | 30.00 | 5.000% | 30.00 | 5.000% | 30.00 |
| B | Butylene Glycol | 3.000% | 18.00 | 3.000% | 18.00 | 3.000% | 18.00 |
| B | Water | 8.850% | 53.10 | 8.850% | 53.10 | 8.850% | 53.10 |
| C | O & R Dispersion BA NSB LP | 10.000% | 60.00 | 10.000% | 60.00 | 7.500% | 45.00 |

TABLE 2-continued

| Phase | Raw Material | Example 2A % | Example 2A Actual (g) | Example 2B % | Example 2B Actual (g) | Example 2C % | Example 2C Actual (g) |
|---|---|---|---|---|---|---|---|
| C | LEI Modifier 200 HL BA NSB LP | 10.000% | 60.00 | 10.000% | 60.00 | 7.500% | 45.00 |
| D | Tris Amino (30% Aqueous) | 1.000% | 6.00 | 1.000% | 6.00 | 1.000% | 6.00 |
| E | Aminat G | 0.400% | 2.40 | 0.400% | 2.40 | 0.400% | 2.40 |
|   |   | 100.00% | 600.00 | 100.00% | 600.00 | 100.00% | 600.00 |

Example 3: Moisturizing Hand Sanitizer

Still another example composition formulated as a moisturizing hand sanitizer was prepared and is summarized in Table 3.

The composition was prepared in discrete parts that were later combined, namely phases, A-D.

In a first vessel, Phase A was prepared. Butylated hydroxytoluene (BHT) was mixed with Ethyl Alcohol until dissolved. Ultrez 20A and Fragrance were added and mixed with a propeller until dissolved and uniform.

Water as Phase B was added and mixed until uniform.

In a second vessel Phase C was prepared. Olive Oil & Revitelix Dispersion BA NSB LP and LEI Modifier 200 HL BA NSB LP, were combined and mixed until uniform.

Olive Oil & Revitelix Dispersion BA NSB includes Water, Glycerin, Preservative, Olive Oil, Echium Seed Oil, Hydrogenated Lecithin and Xanthan Gum.

Phase C was combined with Phases A and B and mixed until uniform.

Phase D, TRIS Amino, was added to adjust the pH to between about 5.5 and about 7.

Anchor mixing was performed to mix out any entrapped air, as necessary.

TABLE 3

| Phase | Raw Material | Example 3A % | Example 3A Actual (g) | Example 3B % | Example 3B Actual (g) |
|---|---|---|---|---|---|
| A | SDA 40-B 190 | 60.800% | 760.00 | 60.800% | 760.00 |
| A | Fresh Fragrance For Serum (Intarome #F-142673) | 0.000% | 0.00 | 0.000% | 0.00 |
| A | Ultrez 20A | 0.350% | 4.38 | 0.350% | 4.38 |
| A | BHT | 0.050% | 0.63 | 0.050% | 0.63 |
| B | Water | 33.500% | 418.75 | 36.000% | 450.00 |
| C | Olive Oil & Revitelix Dispersion BA NSB LP | 2.500% | 31.25 | 1.250% | 15.63 |
| C | LEI Modifier 200 HL BA NSB LP | 2.500% | 31.25 | 1.250% | 15.63 |
| D | Tris Amino 30% Aqueous | 0.300% | 3.75 | 0.300% | 3.75 |
|   |   | 100.00% | 1250.00 | 100.00% | 1250.00 |

In this example, it is believed that the phospholipid acts as a skin conditioning agent and helps supplement the skin barrier along with the Soybean Oil and Echium Seed Oil. A fortified barrier is resistant to water loss and allows the glycerin and butylene glycol humectants to infuse the skin.

Example 4: Hand Sanitizer with Peptide Treatment

An example composition formulated as a hand sanitizer with peptide treatment was prepared and is summarized in Table 4.

Like in Example 1, the composition was prepared in discrete parts that were later combined.

In a first vessel, Butylated hydroxytoluene (BHT) was mixed with Ethyl Alcohol until dissolved. Ultrez 20A and Fragrance were then added and mixed with a propeller until dissolved and uniform.

In a second vessel, Glycerin, Butylene Glycol and Water were combined and mixed until uniform.

In a third vessel, Safflower Oil Dispersion BA NSB LP, O & R Dispersion BA NSB LP, LEI Modifier 200 HL BA NSB LP, and Granactive AGE were added and mixed until uniform.

Safflower Oil Dispersion BA NSB LP includes Water, Glycerin, Preservative, Safflower Oil, Hydrogenated Lecithin and Xanthan Gum.

Granactive AGE is an antiaging skin care complex combining the activity of Palmitoyl Hexapeptide-14 and plant derived glycoconjugates (Goji Berry Extract) for a maximum synergistic effect of rebuilding the skin's extra cellular matrix. It activates multiple rebuilding pathways including collagen biosynthesis, fibroblast proliferation and inhibition of destructive matrix metalloproteinases.

Phases A, B, and C were combined and mixed until uniform.

Phase D, TRIS Amino was added to neutralize to a pH of 6.0-7.0.

Anchor mixing was performed to mix out any entrapped air, as necessary.

TABLE 4

Hand Sanitizer with Peptide Treatment of Example 4

| Phase | Raw Material | Example 4% | Example 4 Actual (g) |
|---|---|---|---|
| A | SDA 40-B 190 | 60.800% | 1216.00 |
| A | Fresh Fragrance For Serum (Intarome #F-142673) | 0.200% | 4.00 |
| A | Ultrez 20A | 0.500% | 10.00 |
| A | BHT | 0.050% | 1.00 |
| B | Glycerin | 5.000% | 100.00 |
| B | Butylene Glycol | 2.000% | 40.00 |
| B | Water | 13.450% | 269.00 |
| C | O & R Dispersion BA NSB LP | 6.000% | 120.00 |
| C | LEI Modifier 200 HL BA NSB LP | 6.000% | 120.00 |
| C | Granactive AGE | 5.000% | 100.00 |
| D | Tris Amino (30% Aq) | 1.000% | 20.00 |
| | | 100.00% | 2000.00 |

Example 5: Creamy Moisturizing Hand Sanitizer

An example composition formulated as a creamy moisturizing hand sanitizer was prepared and is summarized in Table 5.

In a first vessel, Phase A, Ethyl Alcohol, is added and mixed with a propeller.

The components of Phase B were then added to the first vessel, in sequence, Water, Glycerin, Butylene Glycol, and Ultrez 20. During its addition, Ultrez 20 was sifted.

Phase A and Phase B were mixed until uniform for about 30 to about 40 minutes.

Phase C, LEI Modifier 200 HL BA NSB LP and Shea butter Dispersion CCTG BA NSB, was added next while mixing continued until uniform for about 10 to about 15 minutes.

Shea butter Dispersion CCTG BA NSB includes Water, Glycerin, Preservative, Shea Butter, Caprylic/Capric Triglyceride, Hydrogenated Lecithin and Xanthan Gum.

After further homogenization for about three to about 10 minutes, Phase D, AMP ULTRA PC2000 (Aminomethyl-propanediol), was added by portion to bring the pH to between 6.6 and 7.1.

Phase E, Titanium Dioxide 3328, a colorant, was then added mixing continued until uniform for about 10-15 min.

Anchor mixing was performed to mix out any entrapped air, as necessary.

Shea Butter for Texture and Moisturization, along with glycerin and glycols for moisturization. Creamy appearance due to texture of product and titanium dioxide for brighter white appearance.

TABLE 5

Creamy Moisturizing Hand Sanitizer of Example 5

| Phase | Raw Material | Example 5A % | Example 5A Actual (g) | Example 5B % | Example 5B Actual (g) |
|---|---|---|---|---|---|
| A | SDA 40B 200 Proof | 60.800% | 121.60 | 60.800% | 121.60 |
| B | Water | 18.700% | 37.40 | 18.700% | 37.40 |
| B | Glycerin | 5.000% | 10.00 | 5.000% | 10.00 |
| B | Butylene Glycol | 3.000% | 6.00 | 3.000% | 6.00 |
| B | Ultrez 20 | 0.500% | 1.00 | 0.500% | 1.00 |
| C | LEI Modifier 200 HL BA NSB LP | 0.000% | 0.00 | 5.000% | 10.00 |
| C | Shea butter Dispersion CCTG BA NSB | 10.000% | 20.00 | 5.000% | 10.00 |
| D | AMP ULTRA PC2000 | q.s. approx. 0.16%-0.25% pH 6.55-7.1 | | q.s. approx. 0.16%-0.25% pH 6.55-7.1 | |
| E | Titanium Dioxide 3328 (Pigmentary Grade) | 2.000% | 4.00 | 2.000% | 4.00 |
| | | 100.00% | 200.00 | 100.00% | 200.00 |

It should be noted that the terms "first", "second", and the like can be used herein to modify various elements. These modifiers do not imply a spatial, sequential or hierarchical order to the modified elements unless specifically stated.

As used herein, the terms "a" and "an" mean "one or more" unless specifically indicated otherwise.

As used herein, the term "substantially" means the complete or nearly complete extent or degree of an action, characteristic, property, state, structure, item, or result. For example, an object that is "substantially" enclosed means that the object is either completely enclosed or nearly completely enclosed. The exact allowable degree of deviation from absolute completeness can in some cases depend on the specific context. However, generally, the nearness of completion will be to have the same overall result as if absolute and total completion were obtained.

As used herein, the term "comprising" means "including, but not limited to; the term "consisting essentially of" means that the method, structure, or composition includes steps or components specifically recited and may also include those that do not materially affect the basic novel features or characteristics of the method, structure, or composition; and the term "consisting of" means that the method, structure, or composition includes only those steps or components specifically recited.

As used herein, the term "about" is used to provide flexibility to a numerical range endpoint by providing that a given value can be "a little above" or "a little below" the endpoint. Further, where a numerical range is provided, the range is intended to include any and all numbers within the numerical range, including the end points of the range.

While the present disclosure has been described with reference to one or more exemplary embodiments, it will be understood by those skilled in the art, that various changes can be made, and equivalents can be substituted for elements thereof without departing from the scope of the present disclosure. In addition, many modifications can be made to adapt a particular situation or material to the teachings of the present disclosure without departing from the scope thereof. Therefore, it is intended that the present disclosure will not be limited to the particular embodiments disclosed herein, but that the disclosure will include all aspects falling within the scope of a fair reading of appended claims.

What is claimed is:
1. A method for preparing a moisturizing hand sanitizer composition, the method comprising:
a) preparing a first hydrophobe-in-water dispersion by:
i) low energy mechanical processing to obtain a homogenous mixture comprising: water, a humectant, and one or more hydrophobes; wherein the low energy mechanical processing comprises mechanical mixing at ambient temperature and ambient pressure, until an average particle size of the one or more hydrophobes in the mixture is less than 150 microns, to yield an outflow; the mixture having 10% by wt. of the mixture or less of amphiphiles and amphiphilic compounds having a Critical Micelle Concentration (CMC) less than or equal to $10^{-8}$ mol/L, and
ii) subjecting the outflow to high-pressure high-shear processing to form the first, hydrophobe-in-water dispersion, wherein the high-pressure high-shear processing comprises mixing at a temperature from about 15° to about 30° C., a pressure from about 6000 psi to about 31,000 psi, and a shear comprising unaligned shear forces that push a portion of a particle body in the outflow in one specific direction, and another portion of the particle body in the outflow in an opposite direction, causing particles in the outflow to fracture and be broken into smaller particles until at least 79 wt. % of the total particles in the dispersion are ±1.50 standard deviations of an average particle size of the dispersion, the average particle size of the dispersion being from about 150 nm to about 480 nm;
b) preparing an aqueous solvent fluid by combining and mixing water, ethanol or isopropanol, and a humectant; and
c) combining the at least first hydrophobe-in-water dispersion and the aqueous solvent fluid to form the composition, wherein the ethanol or isopropanol in the composition is in an amount from 60% v/v to 95% v/v of the composition;
wherein stability of the combined first hydrophobe-in-water dispersion and aqueous solvent fluid is enhanced when the average particle size of the one or more hydrophobes in the outflow from low energy mechanical processing is less than 150 microns.

2. The method according to claim 1, wherein the ethanol or isopropanol is in an amount that is at least about 62% v/v to 95% v/v of the composition.

3. The method according to claim 2, wherein the ethanol or isopropanol is in an amount that is at most 90% v/v of the composition.

4. The method according to claim 1, further comprising: diluting the amount of ethanol or isopropanol to be at least 60% v/v to at most 90% v/v after adding the at least first hydrophobe-in-water dispersion to the aqueous solvent fluid.

5. The method according to claim 1, further comprising: diluting the first hydrophobe-in-water dispersion with water prior to adding to the aqueous solvent fluid.

6. The method according to claim 1, further comprising:
a) preparing a second hydrophobe-in-water dispersion by:
i) low energy mechanical processing to obtain a homogenous mixture comprising: water, a humectant, and one or more hydrophobes; wherein the low energy mechanical processing comprises mechanical mixing at ambient temperature and ambient pressure, until an average particle size of the one or more hydrophobes in the mixture is less than 150 microns, to yield an outflow; the mixture having 10% by wt. of the mixture or less of amphiphiles and amphiphilic compounds having a Critical Micelle Concentration (CMC) less than or equal to $10^{-8}$ mol/L, and
ii) subjecting the outflow to high-pressure high-shear processing to form the second hydrophobe-in-water dispersion, wherein the high-pressure high-shear processing comprises mixing at a temperature from about 15° to about 30° C., a pressure from about 6000 psi to about 31,000 psi, and a shear comprising unaligned shear forces that push a portion of a particle body in the outflow in one specific direction, and another portion of the particle body in the outflow in an opposite direction, causing particles in the outflow to fracture and be broken into smaller particles until at least 79 wt. % of the total particles in the dispersion are ±1.50 standard deviations of an average particle size of the dispersion, the average particle size of the dispersion being from about 150 nm to about 480 nm; and
b) adding the second hydrophobe-in-water dispersion to the aqueous solvent fluid.

7. The method according to claim 1, wherein the high-pressure high-shear processing is performed at a temperature from about 20° to about 25° C.

8. The method according to claim 1, wherein the high-pressure high-shear processing is performed until at least 85 wt. % of the total particles in the dispersion are ±1.50 standard deviations of the average particle size of the dispersion.

9. The method according to claim 1, wherein at least 85 wt. % of the total particles in the dispersion are ±1.20 standard deviations of the average particle size of the dispersion.

10. The method according to claim 9, wherein the average particle size of the dispersion is from about 160 nm to about 480 nm.

11. The method according to claim 9, wherein the average particle size of the dispersion is from about 170 nm to about 400 nm.

12. The method according to claim 1, wherein the high-pressure high-shear processing is performed until at least 90 wt. % of the total particles in the dispersion are ±1.50 standard deviations of the average particle size of the dispersion.

13. The method according to claim 12, wherein the high-pressure high-shear processing is performed until at least 90 wt. % of the total particles in the dispersion are ±1.20 standard deviations of the average particle size of the dispersion.

14. The method according to claim 12, wherein the high-pressure high-shear processing is performed until at least 95 wt. % of the total particles in the dispersion are ±1.50 standard deviations of the average particle size of the dispersion.

15. The method according to claim 1, wherein the mixture comprises at most 1.5% by wt. of amphiphiles and amphiphilic compounds having a CMC less than $10^{-8}$ mol/L.

16. The method according to claim 1, wherein the mixture comprises at most 0.95% by wt. of amphiphiles and amphiphilic compounds having a CMC less than $10^{-8}$ mol/L.

17. The method according to claim 1, wherein the one or more hydrophobes selected from the group consisting of: anti-acne agents, antimicrobial agents, anti-inflammatory agents, analgesics, anti-erythemal agents, antipruritic agents, antiedemal agents, anti-psoriatic agents, antifungal agents, skin protectants, sunscreen agents, vitamins, antioxidants, anti-irritants, anti-bacterial agents, antiviral agents, antiaging agents, photoprotection agents, wound healing agents, immunomodulators, botanicals, moisturizers, astringents, sensates, anesthetics, tissue healing substances, tissue regenerating substances, amino acids, peptides, minerals, ceramides, hyaluronic acids, skin bleaching ingredients.

18. The method according to claim 1, wherein the one or more hydrophobes is an oil.

19. The method according to claim 1, wherein the one or more hydrophobes is an ester of a fatty acid or an alkane.

20. The method according to claim 1, wherein the mixture further comprises a rheological modifying agent.

21. The method according to claim 1, wherein the aqueous solvent fluid further comprises a rheological modifying agent.

22. The method according to claim 1, wherein the mixture further comprises one or more active ingredient(s).

23. The method according to claim 1, wherein the aqueous solvent fluid further comprises one or more active ingredient(s).

24. The method according to claim 1, wherein the low energy mechanical processing is performed with at least one homogenizer selected from the group consisting of: rotor stator, vacuum homogenization, media mill, and colloid mill.

25. The method according to claim 1, wherein the high-pressure high-shear processing is performed with at least one device selected from the group consisting of: high-pressure and high-shear devices, high-pressure devices, microfluidizers, and sonication.

26. The method according to claim 1, wherein the low energy mechanical processing is performed until an average particle size of the hydrophobes in the mixture is less than 20 microns.

27. The method according to claim 1, wherein the mixture has 4.9% by wt. of the mixture or less of amphiphiles and amphiphilic compounds having a CMC less than or equal to $10^{-8}$ mol/L.

* * * * *